United States Patent [19]
Gomez et al.

[11] Patent Number: 5,873,523
[45] Date of Patent: Feb. 23, 1999

[54] ELECTROSPRAY EMPLOYING CORONA-ASSISTED CONE-JET MODE

[75] Inventors: Alessandro Gomez, Orange; Juan Fernandez de la Mora, New Haven, both of Conn.; Keqi Tang, Beavercreek, Ohio

[73] Assignee: Yale University, New Haven, Conn.

[21] Appl. No.: 808,127

[22] Filed: Feb. 28, 1997

[51] Int. Cl.[6] .................................................. B05B 5/03
[52] U.S. Cl. ............................................. 239/3; 239/704
[58] Field of Search ................................ 239/3, 290, 291, 239/299, 416.5, 423, 424, 690, 692, 704–708; 128/200.14, 203.12

[56] References Cited

U.S. PATENT DOCUMENTS

| | | | |
|---|---|---|---|
| 2,782,074 | 2/1957 | Sedlacsik | 239/290 |
| 3,802,625 | 4/1974 | Buser et al. | 239/704 |
| 4,240,585 | 12/1980 | Sickles | 239/291 X |
| 4,829,996 | 5/1989 | Noakes et al. | |
| 4,842,203 | 6/1989 | Kuhn et al. | 239/299 X |
| 5,115,971 | 5/1992 | Greenspan et al. | 239/3 |
| 5,188,290 | 2/1993 | Gebauer et al. | 239/3 |
| 5,346,134 | 9/1994 | Ma et al. | 239/299 X |
| 5,396,882 | 3/1995 | Zapol | 128/200.14 |
| 5,523,566 | 6/1996 | Fuerstenau et al. | |

*Primary Examiner*—Andres Kashnikow
*Assistant Examiner*—Steven J. Ganey
*Attorney, Agent, or Firm*—Ohlandt, Greeley, Ruggiero & Perle

[57] ABSTRACT

An electrospray apparatus incorporating the invention includes a capillary with an exit for ejecting a fluid, and an electrode positioned downstream from the exit. A gas source is used to establish a region of gas, at least immediately about the exit. A voltage supply creates a potential difference between the capillary exit and the electrode, the potential difference being sufficient to both establish a cone jet mode of operation at the exit of the capillary, to ionize the region of gas about the exit and create a current flow between the exit and the electrode. The current flow exhibits an increased value upon the gas becoming ionized, thus enabling detection of the establishment of a corona. This action creates a corona-assisted cone jet mode of electrospray operation which enables the fluid to disperse into highly uniform sized particles. The preferred gas is carbon dioxide.

10 Claims, 8 Drawing Sheets

ELECTROSPRAY EMPLOYING CORONA-ASSISTED CONE-JET MODE

This Application claims priority from Provisional Patent Application Ser. No. 60/012,520, filed Feb. 29, 1996.

FIELD OF THE INVENTION

This invention relates to an apparatus and method for generation of a fine aerosol through the use of electrospray and, more particularly, a new electrospray method and apparatus which enables achievement of an ultra-fine aerosol of particles, wherein the particles evidence a substantial uniformity of size.

BACKGROUND OF THE INVENTION

Electrostatic means for liquid dispersion in minute droplets are used in a variety of technological applications. In some hybrid systems, electric fields are used just for charging purposes, and atomization is achieved by other means, e.g. pneumatic, ultrasonic, etc. In other systems, the dispersion of the liquid is driven primarily by electric forces, so that atomization and gas flow processes are relatively uncoupled. Those in the latter category are referred to as electrosprays. A background discussion of electrospray can be found in U.S. Pat. No. 5,523,566 to Fuerstenau et al., the disclosure of which is incorporated herein by reference.

Within the electrospray class of atomizers is a particular type characterized by the additional feature of a tight control of the size distribution of the resulting aerosol. Such a system can be implemented by feeding a liquid with sufficient electric conductivity through a conductive tube maintained at several kilovolts relative to a reference electrode positioned a few centimeters away. The liquid meniscus at the outlet of the capillary takes a conical shape under the action of the electric field, with a thin jet emerging from the cone tip. This jet breaks up farther downstream into a spray of fine, charged droplets. In view of the morphology of the liquid meniscus, this regime is labeled as the cone-jet mode.

The cone-jet mode offers not only the appealing feature of droplet monodispersion, but it can produce droplets/particles over a wide size range, from molecular dimensions to hundreds of microns, depending on liquid flow rate, applied voltage and liquid electric conductivity. Especially in the nanometric range, the capability of producing monodisperse particles with relative ease is unmatched by any other aerosol generation scheme. Just as important is the fact that these particles are generated from capillaries with a relatively large bore (e.g., 100 micrometers is a typical figure), which are therefore unlikely to clog.

Another distinctive advantage that the electrostatic approach offers over alternative atomization techniques relates to the presence of a net charge on the surface of the generated droplets. This charge provides a “handle” to guide the particles and to collect them on suitable targets for a variety of purposes. The Coulombic repulsion among droplets prevents any agglomeration by causing droplet self-dispersion.

As the charged droplets evaporate, the electric charge may cause them to subdivide, which eventually creates arbitrarily small drops, residue particles and even ions. If necessary, charge on the droplets can be neutralized after liquid dispersion, using a corona discharge of opposite polarity, a flame, or a radioactive source.

The most important liquid physical properties that govern the electrospray performance are the electric conductivity and the surface tension of the liquid. The electric conductivity defines the range of liquid flow rate over which a) the cone-jet mode can be maintained in a stable manner and b) a uniform droplet size can be produced. Since there is a one-to-one correspondence between liquid flow rate and droplet size, the electric conductivity also governs the range of sizes that can be uniformly produced for a certain liquid. Surface tension intervenes because the voltage required to establish the cone-jet mode is proportional to the square root of this property.

Because of the large surface tension of some liquids, the establishment of stable sprays in air is generally prevented by the occurrence of electric breakdown in the gaseous environment surrounding the spray. The ensuing unsteady corona discharge has destabilizing consequences on the spray behavior and typically prevents operation in the cone-jet mode. For liquids of moderate surface tension, such as aqueous solutions, when air is replaced with $CO_2$, a gas with higher breakdown threshold, operation in the cone-jet mode is possible, as first demonstrated over 80 years ago by the pioneering work of Zeleny. For example, by this approach, droplets of nearly monodisperse size distributions in the 2–8 micrometer diameter range were produced in the case of pure water and hypotonic saline solutions (0.005% NaCl) at flow rates ranging from 7 to 20 microliters/min. Liquid metals, on the other hand, having very large surface tensions have been electrosprayed only in vacuum or inside dielectric liquids.

Electrospray has found numerous applications in a variety of fields. The leading one is Electrospray Ionization (ESI) as a means to introduce, in the gas phase, ions pre-existing in solution, including multiply charged macromolecules. Such ions can be analyzed in a mass spectrometer, through so-called Electrospray Mass Spectrometry (ESMS). What ESMS did to launch the rapidly growing popularity of this technique was to show that large dissolved macromolecules appeared in the gas as multiply charged ions, with sufficient charge to be mass analyzed in instruments with a relatively small mass range, even when the mass of these ions exceeded several millions. Well over 90% of the literature on electrosprays is now devoted to ESMS of large polymers.

The ability of this technique to convert dissolved entities into their charged gas phase counterparts is equally applicable to small inorganic clusters, branched polymers, particles, viruses, or other liquid contaminants of interest.

Other applications have been demonstrated in the laboratory but have yet to find an industrial follow-up, partly because of the relatively small flow rates that the electrospray can deliver. For instance, an electrospray has been shown to be capable of producing droplets of saline aqueous solutions in a size range desirable for drug inhalation therapy, targeted to specific areas of the respiratory tract.

The production of metal clusters and ions by conventional electrosprays typically entails the melting of the metal and the establishment of metal cones under the action of electric fields. High vacuum is usually required because of the high surface tension of the metal. In this way, in the late sixties, the production of $Cs^+$ monomers, dimers and trimers, as well as alkali ions beams was demonstrated. The approach was found to be well-suited for liquid metals of low work functions, whereas higher work functions metals may produce charged droplets and ion clusters at the same time.

Scaling laws for the diameter of electrosprayed droplets indicate that it is possible, from highly conducting solutions, to produce drops with diameters of several tens of nanometers. Even finer particles with controlled and narrow distribution of sizes can be produced by dissolving a nonvolatile solute into an electrosprayable solvent. After electrospray dispersion, the solvent evaporates leaving behind nanometric residues, that can be used for specific applications.

It is an object of this invention to provide an improved electrospray apparatus and method which enables production of highly uniform size particles.

Figure 2:
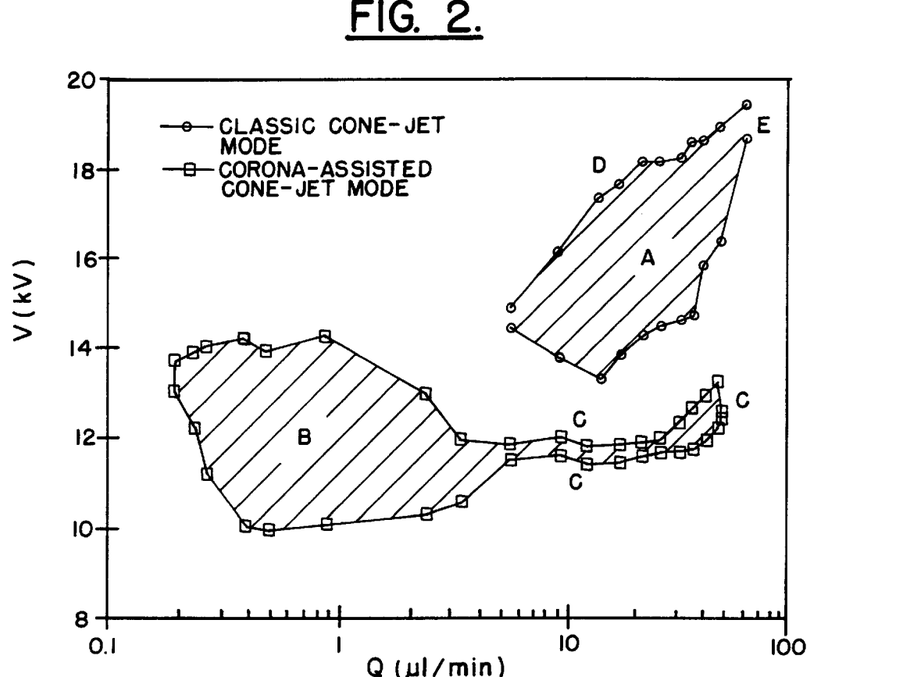

It is another object of this invention to provide an improved electrospray apparat Voltage vs. Liquid-Flow Rate is shown in FIG. 2. One such stability domain, i.e., region A, at relatively high voltage, pertains to the "classic" cone-jet mode that has been extensively studied in the literature. The other, i.e., region B, at relatively low voltage, was discovered by Applicants and named "corona-assisted cone-jet mode", because the characteristic cone-jet morphology is accompanied by a steady corona discharge at the tip of the liquid cone. The onset of the corona assisted mode, as will be shown below (FIG. 8), is accompanied by a substantial increase in current flow between capillary 14 and electrode 18. Accordingly, by proper adjustment of the voltage applied to capillary 14 (while monitoring current flow), the corona-assisted cone jet mode can be reliably established.

Outside regions A and B, three types of phenomena were observed: a) the electrospray was in a pulsating mode with a discontinuous emission of mass from the liquid meniscus (region C in FIG. 2); b) a wild whipping motion of the ligament or the formation of multijets, depending on the liquid flow rate, were observed above the upper bound of the high voltage stability domain (region D in FIG. 2); c) corona discharge set an upper limit of flow rates that could be dispersed in the high voltage mode (60 $\mu$l/min) (region E in FIG. 2). The electrosprays in all these unstable cases were polydispersed.

A comparison between the two stability domains (regions A and B) shows that the corona-assisted domain (region B) extends to flow rates more than one order of magnitude smaller than in the high voltage stability domain. Since the liquid flow rate is the primary variable controlling droplet size, droplets much smaller in diameter and over a broader size range can be generated by operating the electrospray in this new stability domain. At larger flow rates, when the spray can be operated in either one of the two stability domains, operation in the corona-assisted one is only possible over a small interval of applied voltages (300–400 V).

Figure 3A:
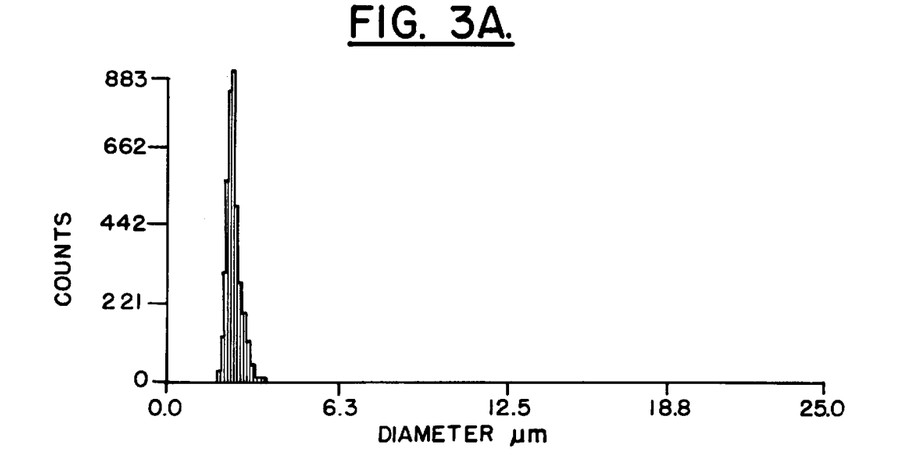
Figure 3B:
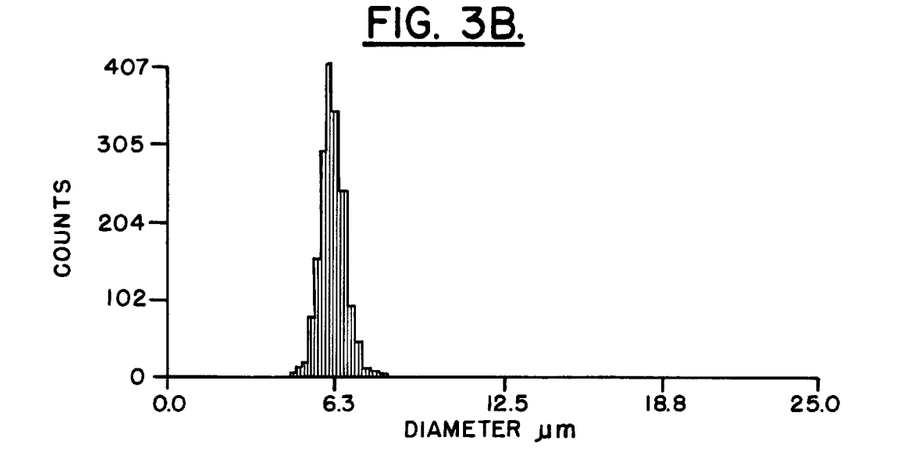
Figure 3C:
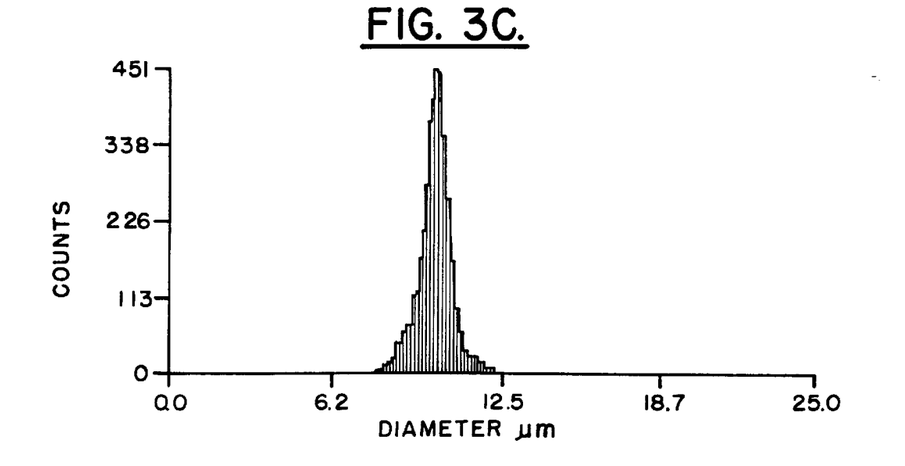

Notice that the size distribution of the generated droplets is narrow regardless of the stability domain in which the electrospray was operated. Phase Doppler Anemometry (PDA), an optical diagnostic technique, was used to determine the droplet size and velocity distributions by laser light scattering. The PDA size measurements were calibrated using different techniques, depending on the droplet size range, so that the overall accuracy of the measurements could be maintained at about 3%. FIGS. 3a–3c show three typical size distributions of water sprays operating at flow rates of 4.67 $\mu$l/min, 19.2 $\mu$l/min and 39.4 $\mu$l/min and voltages of 11.64 KV, 15.2 KV and 16.5 KV, respectively. FIG. 3a was obtained in the corona-assisted stability domain, whereas FIGS. 3b and 3c pertain to the classic cone-jet regime. The mean droplet diameters are 2.43 $\mu$m, 6.11 $\mu$m and 10.1 $\mu$m, and the ratios of standard deviation over mean sizes are 0.12, 0.08 and 0.06, respectively. All the size distributions confirm the monodispersity of the water spray under the cone-jet mode operation.

The appearance of the electrospray was also different in the two domains. A nano-flash shadowgraph system was used to monitor the stability of the electrospray and ensure that it was operated in the cone-jet mode. It consisted of nanosecond flash lamp (Xenon Co.), whose light flashes were focused on the electrospray by a quartz lens, and a stereo zoom microscope (Bausch & Lomb), positioned in a shadowgraph configuration with respect to the lamp. The microscope was coupled with a CCD camera (Pulnix), whose output signal was either shown directly on a TV monitor or recorded by a high resolution VCR and digitized, off-line, by a frame grabber (National Instruments) installed on a Macintosh II computer.

Figure 4A:
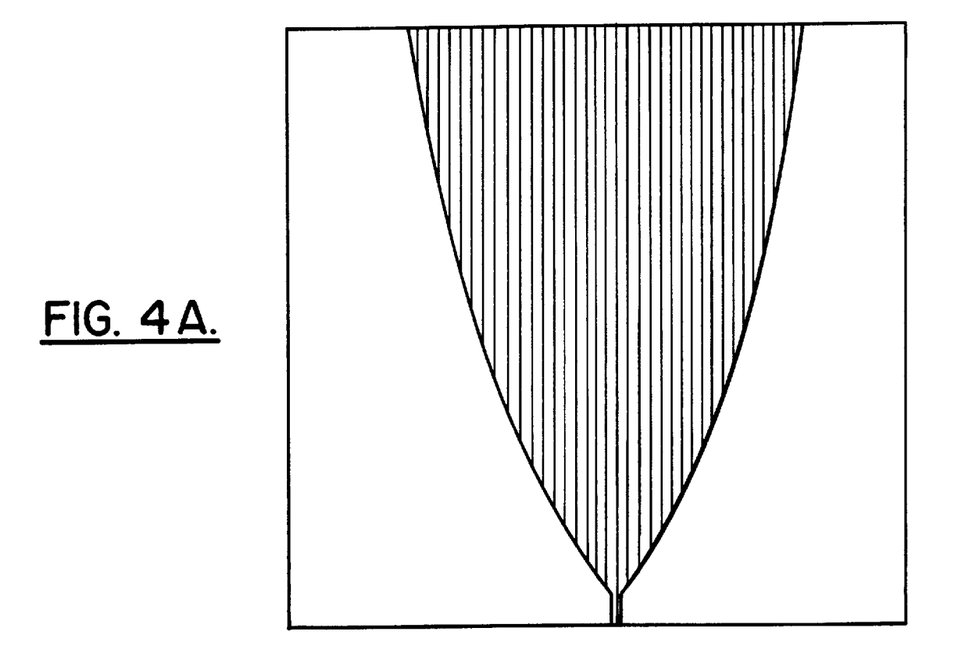
Figure 4B:
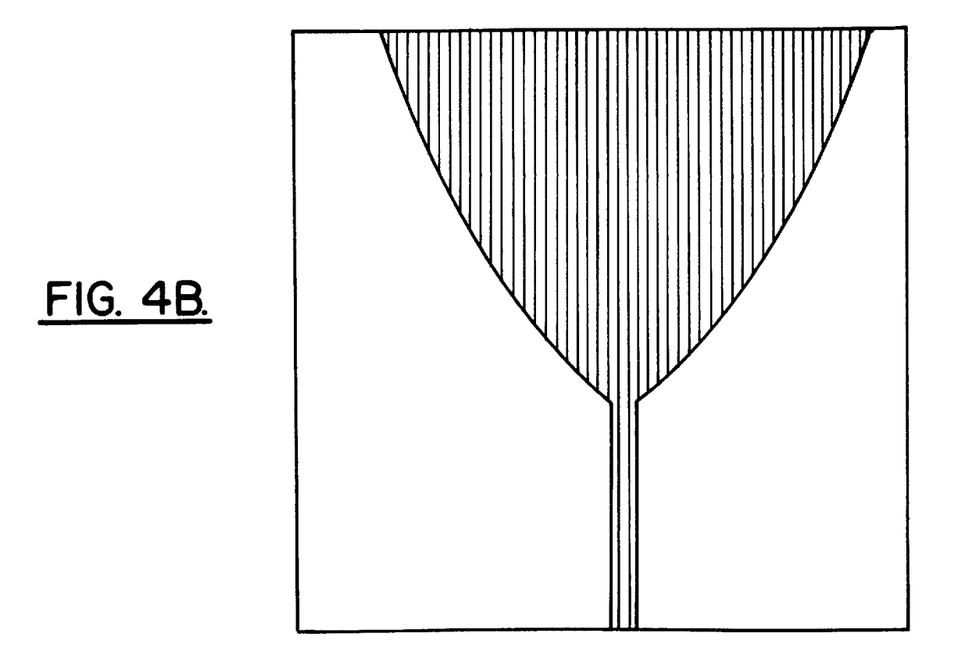

As shown in FIGS. 4a and 4b, at the same liquid flow rate of 5.7 $\mu$l/min, the liquid cone of the spray operated in the low voltage stability domain had a longer cone length and a smaller cone angle (FIG. 4a) as compared with that of the spray operated in the high voltage stability domain (FIG. 4b).

Figure 5:
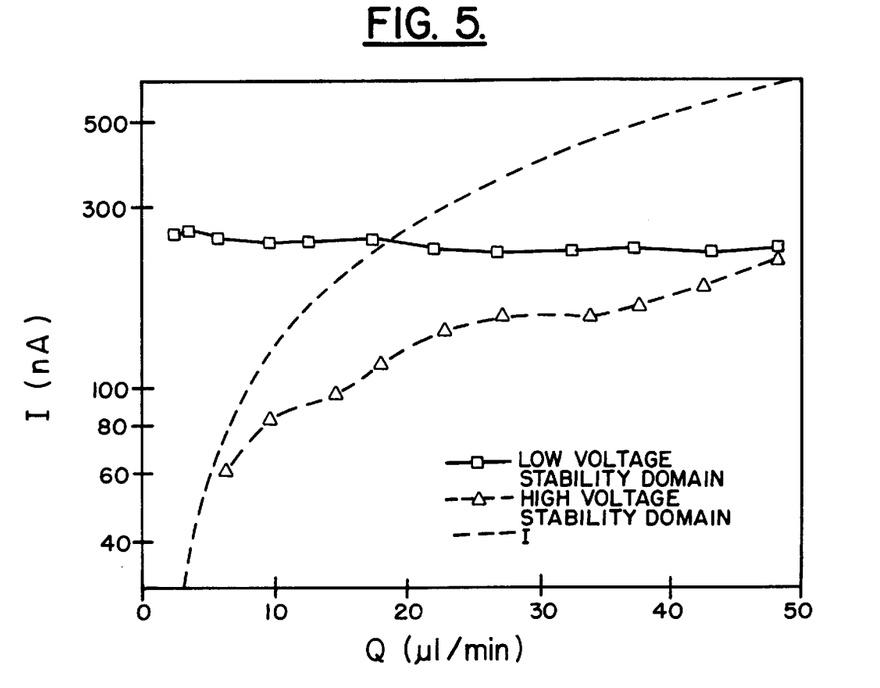

Another significant difference lies in the total electric current measured at the ground electrode. FIG. 5 displays this total current versus liquid flow rate. The spray in the low voltage (corona-assisted) stability domain carries significantly larger electric current than that of the spray in the high voltage (classic cone jet) stability domain at the same liquid flow rate, even though the applied voltage is at least 20% lower than the one in the high voltage stability domain. Also, the difference in transported current between the two domains increases as the liquid flow rate decreases.

Figure 6:
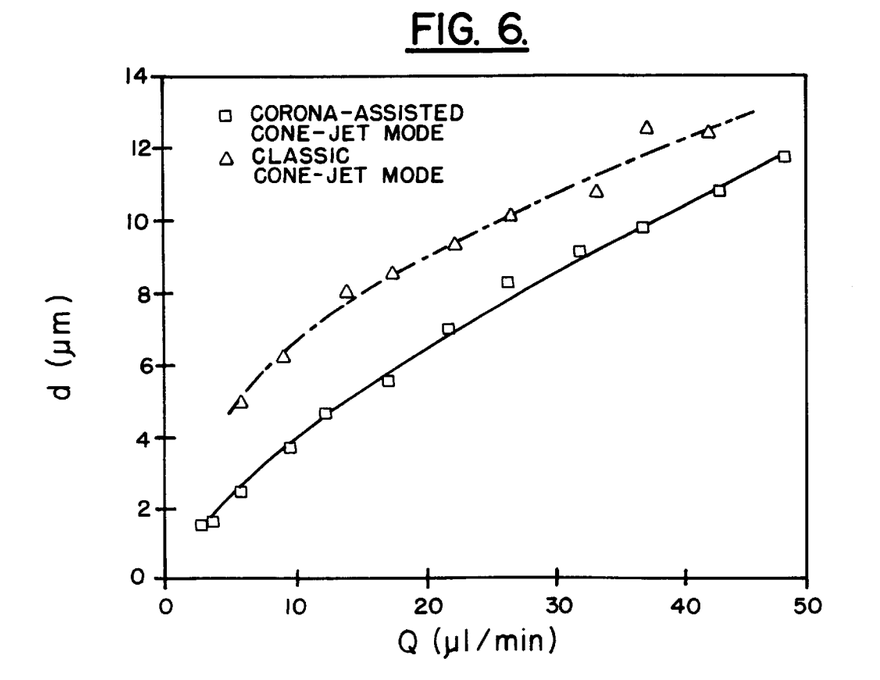

FIG. 6 shows the dependence of droplet size on liquid flow rate for sprays operating in both stability domains at the onset voltage, that is at the minimum voltage required for the cone-jet mode electrospray in each of the two domains. The droplet size of the spray increases monotonically with the liquid flow rate in both cases. By varying the liquid flow rates from 5.8 $\mu$l/min to 42.4 $\mu$l/min in the upper stability domain, droplets with diameters ranging from 5 $\mu$m to about 12 $\mu$m can be generated. Stability problems of the spray at flow rates smaller than 5.8 $\mu$l/min prevented the generation of smaller droplets in this domain.

The consequence of operating solely in the classic cone-jet mode, as per prior art, is that if one needs to broaden the droplet size range, for example to cover the entire size range relevant to applications to targeted delivery of a drug by inhalation (2~8 $\mu$m), the electric conductivity of the water has to be adjusted by varying the concentration of NaCl in the solution. Conversely, in corona-assisted cone-jet mode there is no need to change the liquid composition. The entire range of 2~8 $\mu$m can be directly generated by the water spray. In fact, the minimum droplet diameter shown in FIG. 6 for the low voltage stability domain only reflects range limitations of the Phase Doppler diagnostic system (Dantec).

Extrapolating the size-flow rate dependence at the low flow rates on the basis of the results in FIG. 2, it is expected that even submicron droplets can be directly produced in this domain.

As also shown in FIG. 6, the droplet size of the spray increases at fixed flow rate when the spray operation switches from the corona-assisted cone-jet mode to the high voltage stability domain. This finding may help explain the presence of corona at relatively low voltage levels. Since the favorable site for the initiation of the discharge should be a region at a high potential and with a very small radius of curvature, a likely candidate must be the tip of the liquid cone from which droplets are generated. The diameter of the jet emerging from the cone tip is known to be proportional to the droplet diameter. Thus, despite the lower voltage level, local electric fields near the jet may still be higher for the sprays operating in the corona-assisted cone-jet mode because of the smaller radius of curvature of the jet as compared to electrosprays in the high voltage, "classic", cone-jet mode. Droplets obtained in the two domains differ by a factor of two in size at low flow rates and by about 20% at large flow rates. Also, as flow rate is increased, droplet size and liquid jet diameter also increase. Both of these two observations imply a diminished likelihood of corona as liquid flow rate increases. Consequently, it is expected that the corona contribution to the total current decreases, as the liquid flow rate increases. Thus, the total current measured in the classic cone-jet mode and in the corona-assisted cone-jet mode should eventually merge, as the data in FIG. 5 indicate.

Figure 7A:
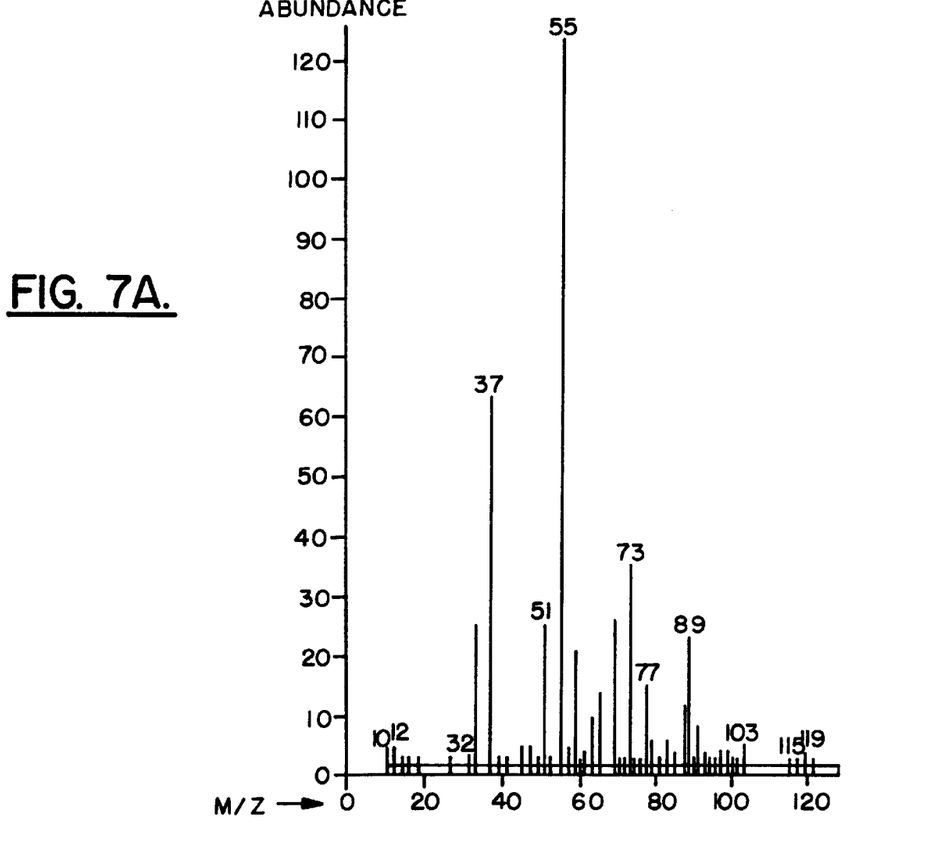
Figure 7B:
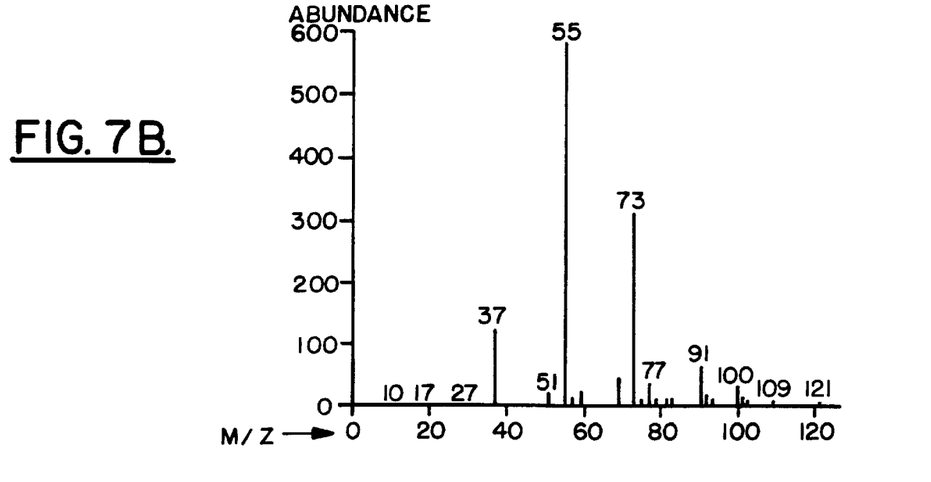

If gas phase ions contribute to the total current in the low voltage stability domain, especially at small liquid flow rate, some form of corona, that is a stable electric discharge that does not disrupt the cone-jet electrospray, must occur in $CO_2$. Initial efforts to separate directly gas-phase ions from charged droplets in the spray, by imposing an additional ion sweeping electrode in the spray system, failed because of the comparable mobility between the ions and the charged droplets. However, the hypothesis of gas-phase ionization was corroborated by the two independent methods:

1) When the $CO_2$ sheath gas was replace by SF6, a gas having a higher electric breakdown threshold, the high voltage stability domain, the one without discharge, was affected neither in stability nor in the total electric current measured at the ground electrode. On the other hand, the spray operating in the low voltage stability domain became unstable at all tested flow rates. The liquid cone began to pulsate, leading to very broad droplet size distributions, and the electric current dropped by one order of magnitude;

2) An independent and more direct verification of the presence of $CO_2$ corona was obtained by coupling the electrospray with a mass spectrometer, as is customarily done in electrospray ionization. FIGS. 7a and 7b show the mass spectra of the electrosprays operated at same flow rate of 5.7 $\mu$lit/min but in different stability domains. Both spectra exhibit four dominant peaks at m/z equal to 37, 55, 73 and 91, that can be assigned to protonated water clusters, namely $(H_2O)nH^+$ with n varying from 2 to 5. Smaller peaks, also present in both regimes, at m/z equal to 59 and 77 can be attributed to $(H_2O)_2Na+$ and $(H2O)_3Na^+$. However, in the low voltage stability domain, as shown in FIG. 7a, some characteristic peaks at m/z equal to 45, 88 and 89 can be assigned to $(CO_2)H^+$, $(CO_2)_2^+$ and $(CO_2)_2H^+$ respectively. Such peaks were not detected when the voltage applied to the electrospray was raised to shift domain to the high voltage mode (FIG. 7b). In performing this comparison, experimental conditions were identical, except for the different voltage applied to the metal capillary from which the liquid was ejected. Therefore, it is justifiable to compare directly the two spectra in FIG. 7. Such comparison conclusively confirms that the spray operated in the low voltage stability domain is indeed accompanied by gas ionization, which justifies the labelling as corona-assisted cone-jet mode.

Notice that this regime is different from those discussed by Cloupeau, Journal of Aerosol Science, Vol. 25, p 1143, (1994), since the steady corona is established at voltage levels lower than the critical one for the "classic" cone-jet mode. It also offers distinctive advantages in terms of sprayable flow rates and droplets sizes, as shown in FIG. 6. The discharge current in the spray was relatively small compared to that of a typical corona discharge. The current was stable, as indicated by the constant readings of either the pico-ammeter or the oscilloscope that were connected to the ground electrode, and no visible glow was detected in the present experiments. In view of its stability, the electric discharge should be classified as a pulseless glow corona, also referred to as Townsend discharge. In the present experiment, however, the corona, in addition to being pulseless, was also glowless, at least in the visible, since $CO_2$ vibrational relaxation is known to occur at infrared wavelengths.

Figure 1A:
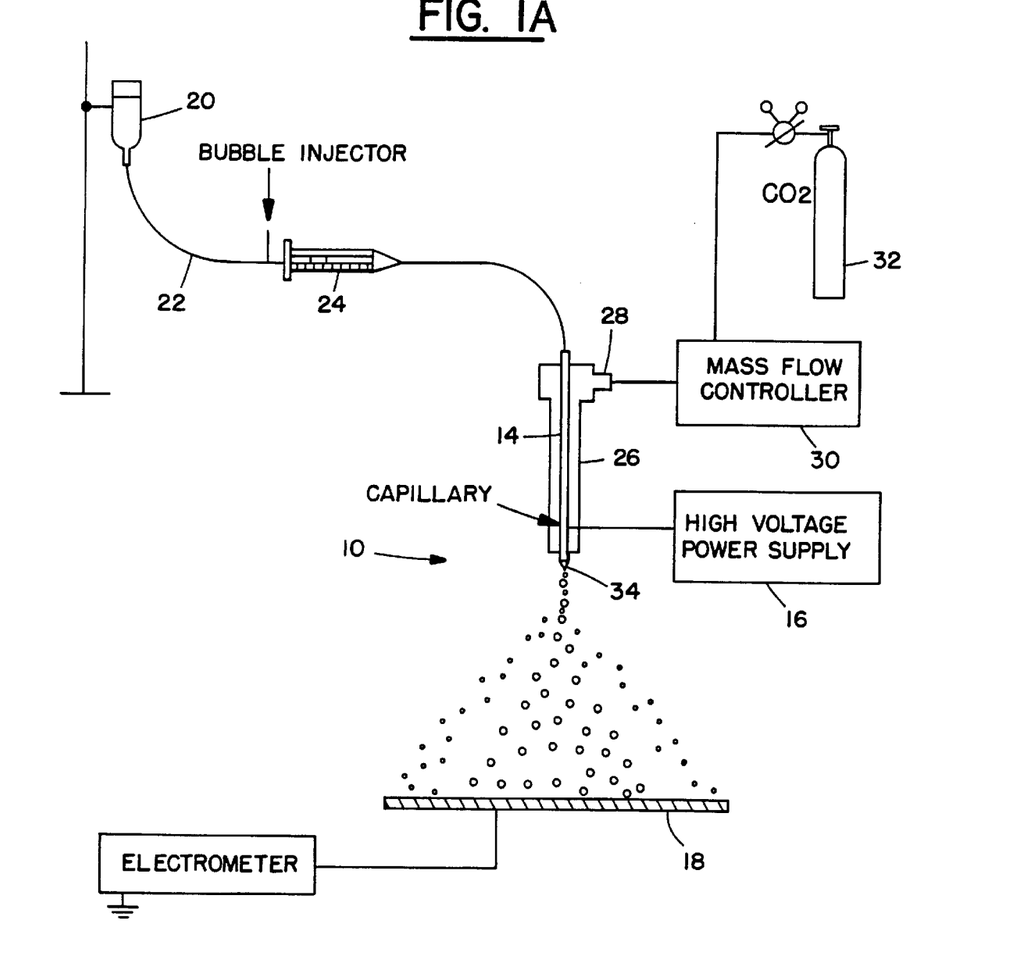
Figure 1B:
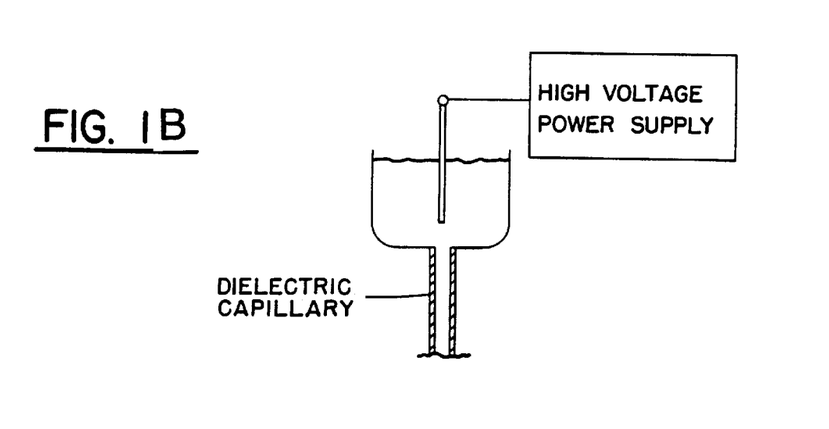
Figure 8:
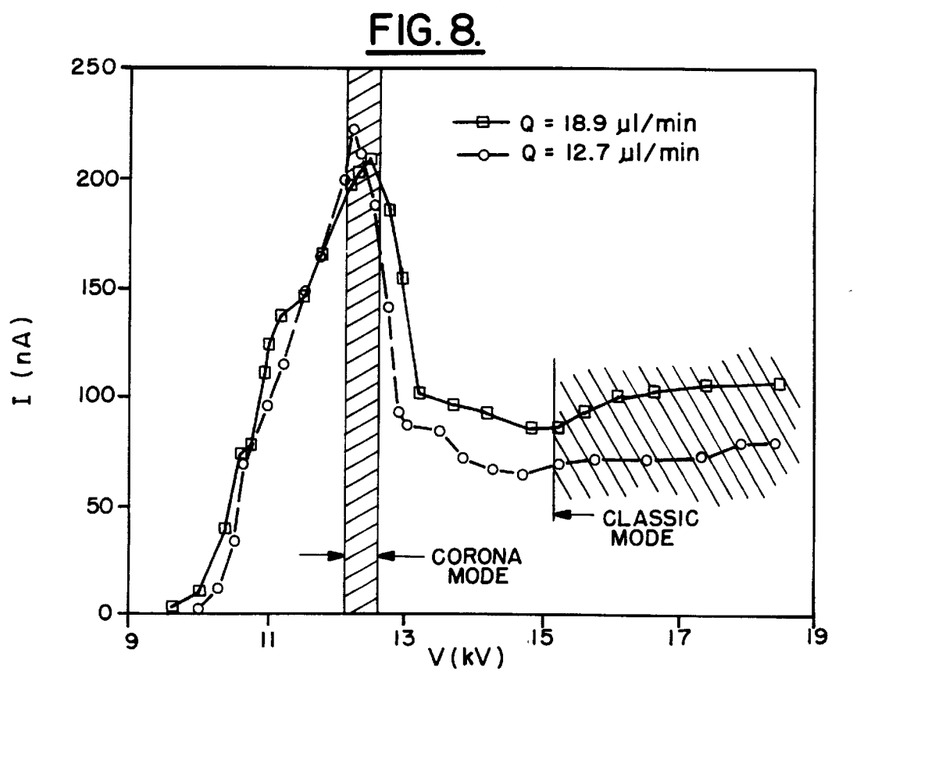

Once the existence of corona is conclusively established, it is worthwhile to compare the current-voltage signatures in electrosprays at constant flow rates and contrast them with that typical of corona discharges from solid electrodes, i.e. in the absence of a spray. FIG. 8 shows two such curves, corresponding to two liquid flow rates, 12.7 $\mu$l/min and 18.9 $\mu$l/min respectively. In both cases, note that as the applied voltage increases, so does the current, up to a peak value in correspondence of the corona-assisted cone-jet mode. Further increases in voltage cause a precipitous drop in current by more than a factor of two. At even larger voltages, specifically for value greater than about 15 KV for the electrode configuration of FIG. 1, the current starts to rise again as the electrospray is brought into the "classic" cone-jet mode. Notice that the current is steady only in the two cone-jet modes (dashed areas in the figure). Outside those regions, the current fluctuates wildly and the reported data represent only averages.

The current-voltage signatures in FIG. 8 are in sharp contrast with the typical behaviors of solid metal electrodes in the point-plane configuration. In the latter case, the current is a monotonically increasing function of voltage as the voltage in the various corona regimes is increased up to the spark breakdown voltage.

The corona-assisted mode of electrospray operation has the important consequence of decreasing by more than one order of magnitude, the minimum flow rate and consequently, the minimum droplet size that can be electrosprayed, and results in the production of monodisperse water droplets with diameters anywhere from several micrometers down to the submicron range.

The explanation for this observation is as follows. If one assumes that charging of the liquid droplets in the classic cone-jet mode is caused by ion separation in the liquid, the maximum current that the electrospray can transport at a given flow rate, $I_{max}$, is achieved when this separation is complete, that is, when all counter-ions brought by the liquid into the meniscus are neutralized at capillary tip 34. If one assumes that the primary ions in the cone of the deionized water are singly charged $Na^+$ and $Cl^-$, knowing the electric conductivity and the liquid flow rate, one can estimate the maximum current achievable by the spray. Accordingly, an ion concentration $n_i=4.87 \times 10^{21} m^{-3}$ can be reached in the liquid under complete ion separation conditions, which corresponds to a maximum volume charge density $n_q=780$ $C/m^3$ and an estimated maximum current, $I_{max}=n_qQ$, where Q is the liquid flow rate.

$I_{max}$ is plotted in FIG. 5 as a dotted line. As anticipated, this curve lies always above the current curve for the high voltage stability domain corresponding to the classic cone-jet mode. At the very smallest flow rate these two curves would eventually intercept, which implies that in the classic cone-jet mode the minimum flow rate is physically determined by the attainment of this limit. Consequently, also the minimum droplet diameter is physically determined in the classic cone-jet mode when this maximum current limit is reached. On the other hand, this limit can be overcome if other external mechanisms, such as gas-phase ionization (corona) are used to supply charge to the tip of the meniscus of a polarity opposite to the of the ions in the liquid phase in that region.

A likely mechanism able to extend the lower flow rate range in the newly discovered regime is now clear. In the presence of corona, ions of both polarities and electrons are formed in the gas phase. The negative charge carriers are then attracted into the apex region of the liquid meniscus where the field is most intense, and are then absorbed into the liquid phase, providing a means to assure charge neutrality within the meniscus. An alternative interpretation can be offered in terms of electric fields, i.e., the condition of complete ion separation in the cone corresponding to the maximum tolerable internal field in the liquid conical meniscus. Beyond these conditions, that is at even lower flow rates, instabilities in the liquid cone can be avoided in the presence of corona, if the negative charge carriers in the gas-phase can be absorbed into the liquid phase, thereby mitigating the internal electric field.

To the best of the Applicants' knowledge, Applicants are the first to create this novel regime, in which the cone-jet mode of the electrospray co-exists with a mild corona discharge. The important consequence of establishing such a regime is that one may circumvent limitations in the minimum flow rate and minimum droplet diameter that can be electrosprayed in the cone-jet mode, for a given liquid electric conductivity. Furthermore, the corona-assisted regime may provide a supplementary ionization source.

The existence of multiple connected stability domains in the voltage/flow-rate plane is not unique to the water-$CO_2$ system. Indeed, experiments with other liquids, for example heptane in air, showed similar results, even in the meniscus morphology (FIG. 4). However, no gas-phase ionization was associated with the new domain for the heptane-air system, nor any distinctive advantages in terms of droplet sizes or sprayable flow rates were found.

It is likely that crucial to the establishment of the corona-assisted cone-jet mode of the electrospray is that the gas surrounding the capillary from which the spray originates has the following feature: its breakdown potential at which a mild corona, as described above, occurs must be approximately of the same value as the electric field that is necessary to establish the cone-jet mode. For example, it is likely that with liquids of sufficiently high surface tension, such as water, the corona-assisted cone-jet mode would be observed with other gases or gaseous mixtures with dielectric strength comparable to that of $CO_2$. For example, an Air/$SF_6$ mixture in appropriate concentrations could be one such mixture. Conversely, if instead of water, a liquid of smaller surface tension were to be sprayed in air, mixing air with either Helium or Argon, both gases with relatively low dielectric strength, could promote ionization and establish the corona-assisted cone-jet mode. Yet another means of varying the dielectric strength of the surrounding gas would be varying the pressure of the gas in which the electrospray is formed by housing the electrospray apparatus in a controlled-pressure chamber.

A second set of experiments was performed to assess the advantage of operating in the newly discovered corona-assisted mode in Electrospray Ionization (ESI), the leading application of electrospray, as documented by Tang and Smith (International Journal of Mass Spectrometry and Ion Process, 1997, in press). The experimental system entailed adapting the system of FIG. 1 to the inlet of a mass spectrometer which is of conventional design. The electrospray ionization source included a stainless steel capillary (I.D.=177 $\mu$m, O.D.=355 $\mu$m) charged to high electric potential relative to a counter electrode positioned typically between 5 to 10 millimeters away from the tip of the metal capillary. The counter electrode was either a brass disk connected to a picoammeter (Keithley Instruments) for the measurement of total electric current carried by electrospray, or the sampling aperture of the mass spectrometer. The liquid flow was controlled and metered using a microsyringe pump. Coaxial with the capillary, a sheath flow of $CO_2$, metered using a gas rotameter, was applied to isolate the capillary tip from the air environment in an effort to suppress the onset of corona discharge. A $N_2$ countercurrent shielded the mass spectrometer chamber from air and aided in the desolvation process. Six different samples, as listed in Table 1, were used in the experiments which varied molecular weight by over an order of magnitude (from –600 $\mu$ to >12,000 $\mu$).

TABLE I

Sample Solution Properties

| Sample | Molecular Weight (u) | Concentration in solution (mg/ml) | Electric conductivity ($\Omega^{-1} \cdot cm^{-1}$) |
|---|---|---|---|
| Phe-Met-Arg-Phe Amide | 598 | 0.02 | $1.508 \times 10^{-5}$ |
| Bradykinin | 904 | 0.02 | $1.365 \times 10^{-5}$ |
| Agiotensin I | 1282.5 | 0.05 | $5.594 \times 10^{-6}$ |
| Insulin B | 3495.9 | 0.10 | $1.475 \times 10^{-5}$ |
| Ubiquitin | 8565 | 0.10 | $7.891 \times 10^{-6}$ |
| Cytochrome C | 12327 | 0.10 | $9.457 \times 10^{-6}$ |

Deionized water, whose electric conductivity was measured at $3.5 \times 10^{-6}$ $\Omega^{-1} \cdot cm^{-1}$, was used as the solvent for all sample solutions. Table 1 gives also the sample concentrations and electric conductivities. All solution electric conductivities were larger than the conductivity of pure water to within one order of magnitude, which allowed both cone-jet mode electrosprays to be established at microliter per minute liquid flow rates.

Mass analysis was performed using a Sciex TAGA 6000E mass spectrometer having a source part modified to incorporate an additional stage of differential pumping.

The first quadruple (Q1) scan mode of the instrument was used for all experiments. Prior to mass spectrometric measurements, electrosprays of all sample solutions were first evaluated using a simplified configuration in which the mass spectrometer inlet was replaced by a grounded metal plate. A microscope was used to monitor the electrospray operation and the total electric current for both corona-assisted cone-jet mode and classic cone-jet mode was measured by the picoammeter at selected liquid flow rates. An electric current increase, by a factor of three to four, depending on the liquid flow rate, was observed upon switching the electrospray from the classic cone-jet mode to the corona-assisted cone-jet mode at a given liquid flow rate, consistent with the results of FIG. 5.

These tests determined the optimum experimental conditions for both applied voltage and liquid flow rate. Both cone jet electrosprays were found to be easily established at liquid flow rates of 1 to 5 $\mu$l/min with the applied voltage of 3 to 4 KV. The sample solutions were then examined by ESI-MS (Electrospray Ionization Mass Spectrometry) at the predetermined voltage and flow rate conditions for both corona-assisted cone-jet mode and classic cone-jet mode electrosprays. The spray current was monitored in all cases to ensure the expected mode of electrospray operation. Each spray mode was examined several times after slightly varying the spray location relative to the entrance orifice of the mass spectrometer so that optimum sensitivity for each was achieved.

Figure 9A:
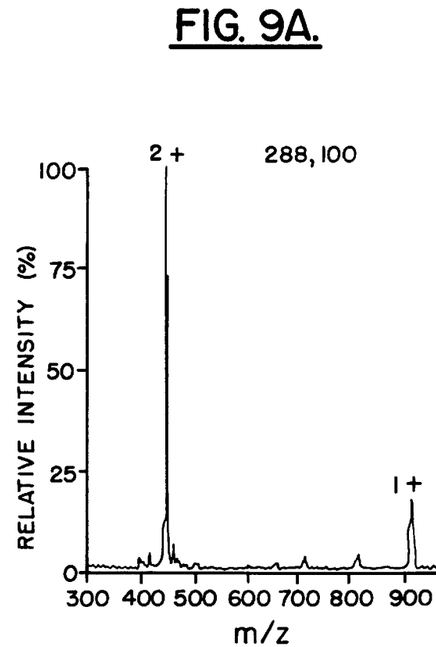
Figure 9B:
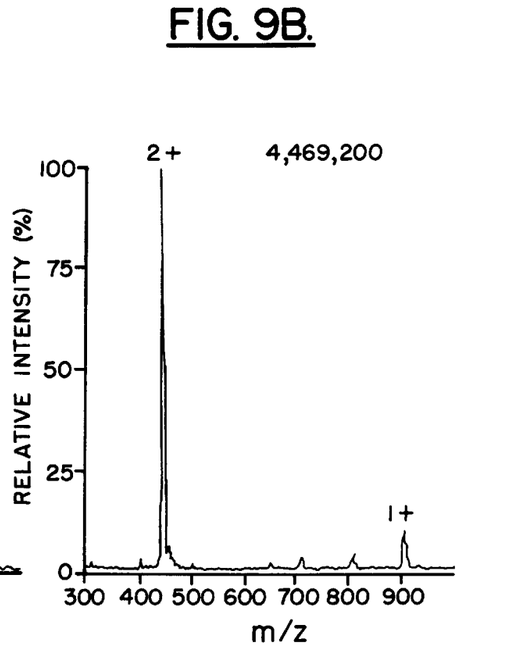
Figure 9C:
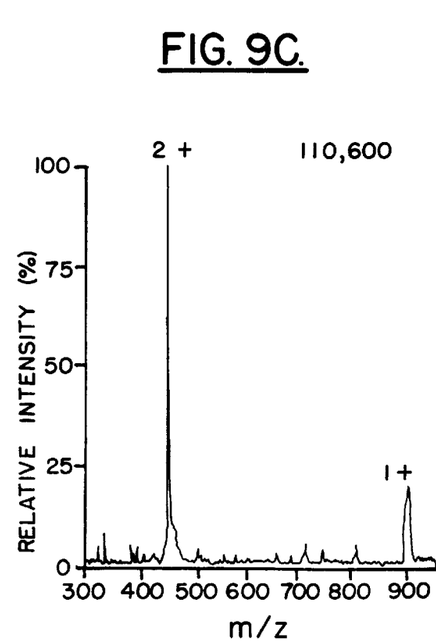
Figure 9D:
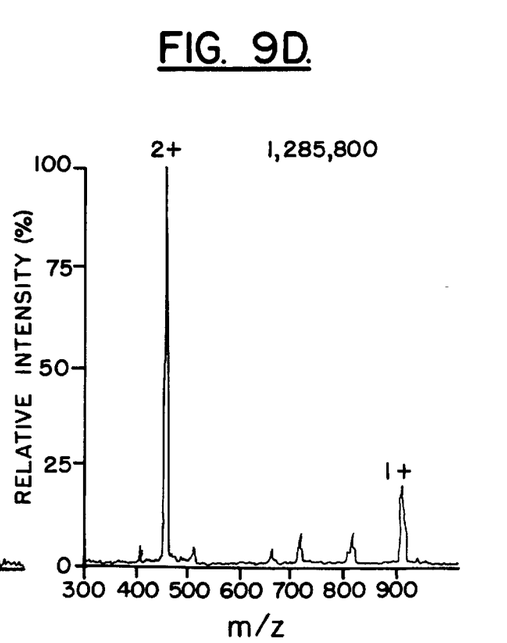
Figure 10:
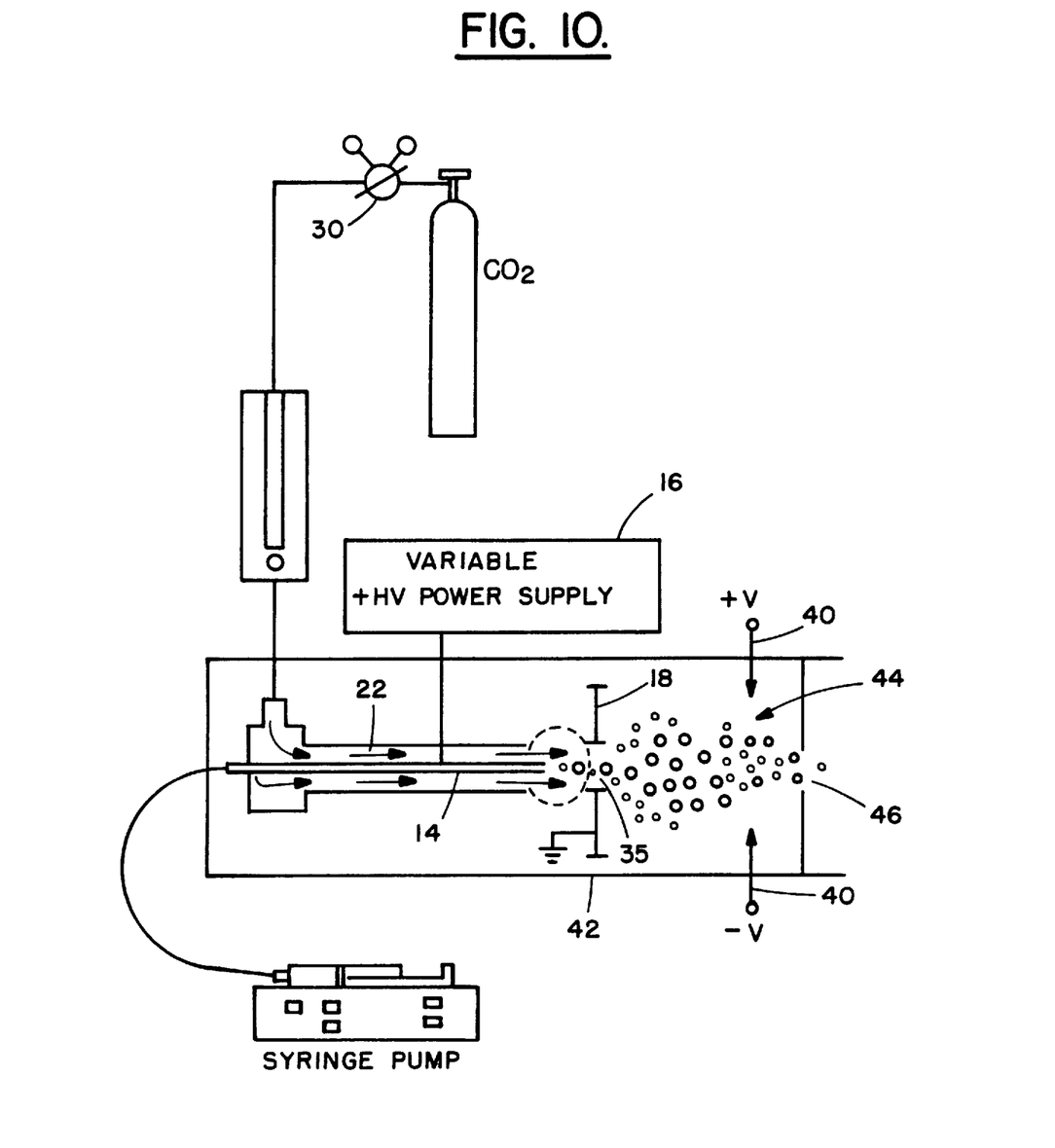

FIGS. 9(a)–9(c) show mass spectra of a Bradykinin solution for the two electrospray modes at liquid flow rate of 1 $\mu$l/min and 5 $\mu$l/min. The signal levels for the two electrospray modes differ by more than an order of magnitude. Thus, a signal increase is achieved by simply switching electrosprays from classic cone-jet mode (FIGS. 9(a) and 9(c) to corona-assisted cone-jet mode (FIGS. 9(b) and 9(d)).

This enhancement was substantially independent of the liquid flow rate (or droplet diameter). As also shown by FIG. 9, the measured signal intensities increase for both spray modes as the liquid flow rate decreases because of more effective droplet desolvation at lower liquid flow rates.

The sensitivity enhancement for the corona-assisted cone-jet electrosprays was further evaluated using compounds of varying molecular weight. For consistent comparison, all the spectra were collected under the same mass spectrometer conditions. Table 2 give ion counts for the most abundant peak for each of the six compounds at liquid flow rate of 3 $\mu$l/min, and again shows an approximate order of magnitude enhancement of measured ion abundances in the corona-assisted cone-jet mode.

TABLE II

Signal Gain upon Transition to Corona-Assisted ESI
at Fixed Liquid Flow Rate of 3 ul/min

| Sample | ESI | Corona-Assisted ESI |
|---|---|---|
| Phe-Met-Arg-Phe Amide | 62,300 | 1,726,100 |
| Bradykinin | 155,600 | 1,943,900 |
| Agiotensin I | 242,000 | 4,559,600 |
| Insulin B | 125,200 | 1,311,900 |
| Ubiquitin | 148,500 | 1,197,300 |
| Cytochrome C | 119,100 | 2,411,700 |

The data in FIG. 9 and Table 2 indicate that the corona-assisted cone-jet mode electrospray can significantly improve the signal sensitivity. This sensitivity gain appears independent of liquid flow rate. It was also observed, as indicated by FIG. 9, that the sensitivity enhancement occurs nearly uniformly across the spectra.

APPLICATIONS OF THE INVENTION

A. Mass-Spectrometry by hybrid APCI-ESI (Atmospheric Pressure Chemical Ionization-ElectroSpray Ionization).

ESI, as described above, does not work for certain chemical compounds. An alternative technique, APCI, entails dispersing a liquid in which the analyte is dissolved by any nebulization method and then, after significant evaporation of the resulting droplets, exposing them and/or the analyte residue to a corona discharge. The establishment of the corona-assisted cone-jet regime will enable the simultaneous implementation of the two techniques. To be sure, the corona currents generated in this method are modest (200–300 nA). (See FIG. 5). However, they are generated locally, near the tip of the cone-jet. Consequently, current densities may be sufficient for the gas-phase ions to reach the analyte molecule in their flight towards the mass-spectrometer.

B. Mass-Spectrometry by ESI, especially at ultra-low flow rates

A method developed in prior art enables the electrospraying of solutions at a few nanoliters per minute from capillaries of a few microns in diameter. This approach has become widely used for mass spectrometry applications, because it permits extraordinary sensitivities with exceedingly small analyte samples. Recent experiments show that the increased sensitivity resulting from operating at low flow rates tapers off below about 100 nl/min. This flow rate is accessible in the corona-assisted mode using the same large bore capillary (100–200 mm) that is used in conventional ESI. Consequently, a single ESI source can be used over a very broad range of conditions, without the need to develop special electrodes for ultra-low flow rate applications. Most importantly from a practical viewpoint, clogging problems would be drastically reduced or eliminated.

C. Drug Inhalation Therapy

For targeted drug inhalation, operation in the classic cone-jet mode at the minimum flow rate leads to the generation of droplets measuring approximately 5 micrometers in diameter in the case of distilled water with a liquid electric conductivity of 1.02 $10^{-6}$ $W^{-1}$ $cm^{-1}$. This size is well beyond the range for optimal deposition in the alveoli (i.e., 2 to 3 micrometers). Somewhat smaller droplets can be sprayed only by increasing the solution conductivity, as in the case of saline solutions. However, such solutions are difficult to electrospray stably.

In the corona-assisted mode, on the other hand, droplets with the critical size of 2 micrometers can be produced without the need of hypotonic saline solutions (0.005% NaCl). FIG. 10 illustrates the adaptation of the electrospray instrument of FIG. 1 to an inhalation therapy application. For such an application, it is desired that the electrospray particles exhibit a neutral charge. Droplets produced in the electrospray, on the other hand, carry a substantial electric charge. To achieve electric neutralization the droplets are directed to grounded electrode 18, pass therethrough via orifice 35 and into a region in which a plurality of needles 40 are positioned. Needles 40 extend into enveloping enclosure 42 and have applied thereto, a high potential of polarity opposite to that of the electrospray. As a result, a corona is created in region 44 which acts to neutralize a positive charge on the electrospray particles which exit via opening 46.

Recently, in collaboration with a group at Johns Hopkins University, the efficacy of the corona-assisted cone jet delivery system on human volunteers was tested using radioactive labeling of the aerosol. Gamma scintillation counting suggested that more than 85% of the inhaled droplets reached the alveolar region. Furthermore, as clearly shown by the experience of the mass-spectrometry community with Electrospray Ionization, the technique is sufficiently "soft" to cause no damage to the labile proteins and peptides that need to be inhaled.

D. Production of metal clusters

The establishment of the corona-assisted regime may simplify dramatically the production of metal clusters and ions using the electrospray and, equally importantly, broaden the selection of metals and related compounds from which clusters can be formed. It should also increase dramatically the size of metal ion clusters that can be generated reproducibly. To understand how this comes about, one needs consider that the minimum flow rate in the classic cone-jet mode for the water sprays considered corresponds to complete ion-separation in the liquid phase, with the counter ions being neutralized at the electrode from which the liquid is ejected and homopolar ions being released in the emitted droplets. Using, for example, a metal salt precursor, pure metal ions could be released from such a source. But, this condition is inherently unstable in the classic cone-jet mode: a slight decrease in flow rate would cause instabilities; a slight increase would imply that ion separation in the cone is not complete. In the corona-assisted mode, stable electrospray operation can be maintained down to a minimum flow rate that is more than one order of magnitude smaller than the minimum flow rate in the classic cone-jet mode. Throughout this flow rate range, ion separation would be complete in the liquid phase. Consequently, it would be sufficient to dissolve a metal salt in water to release droplets containing metal ions of homopolar charge. Upon drying of the solvent, e.g. water, metal ion clusters would be left as residues. Alternatively, at sufficiently low flow rates it is also possible that ion clusters are directly released.

Other approaches to generate metal clusters from Taylor cones held in a vacuum have been known for quite some time. They are limited, however, by the need to operate in a vacuum, as well as by the exceedingly high electrical conductivity characteristics of liquid metals. This last factor makes liquid metal ion sources ideal to produce metal ions and very small clusters. However, it leads to rather broad size distributions when the system is intended to produce nanosize drops. The new approach based on liquid electrolytes can operate at atmospheric pressures, has at its disposal a wide variety of metal-containing salts, and allows close control of monodispersity and size from supermicron drops down to nanometer dimensions. Once produced, the clusters could be used in a variety of applications including "writing" of patterns with nanometric resolution, thin film deposition of metal clusters on surfaces or on a matrix, co-deposition of quantum dots with another hot material to form composite thin films, etc.

E. Gas-phase dispersion of narrowly distributed nanometric particles of high purity Many techniques able to produce highly monodisperse nanoparticles do so in solution. Bringing these dissolved nanoparticles into the gas phase is often desirable, either to size them or to form useful materials via gas phase methods. In either case, it is important to atomize the liquid suspension into very small droplets as otherwise nanoparticle agglomerates would form and nonvolatile impurities in the solvent drops would end up on their surface as contaminants. The electrospray is ideally suited to achieve the desired ultrafine atomization. However, very fine atomization in the classical cone jet requires the addition of electrolytes to the liquid to attain a high electrical conductivity. This has two undesirable effects. First, it often destabilizes the sol, leading to coagulation. Secondly, the added electrolyte tends to increase the level of surface contamination of the dried nanoparticles. Accordingly, the discovery of the corona-assisted mode and the ensuing reduction of the minimum sprayable flow rate may permit the elimination of the electrolyte-doping step and would, consequently, result in purer and less agglomerated nanoparticles.

F. Other Applications involving ultrafine atomization

The advantages just discussed of ultrafine atomization free from the high conductivity requirement of the classical cone jet clearly allow a broad range of uses of the corona assisted mode. Some examples are in sprays for insect killer or odor dispensers, where the efficient use of the liquid sample requires small initial droplet size.

It should be understood that the foregoing description is only illustrative of the invention. Various alternatives and modifications can be devised by those skilled in the art without departing from the invention. Accordingly, the present invention is intended to embrace all such alternatives, modifications and variances which fall within the scope of the appended claims.

We claim:

1. An electrospray apparatus comprising:

a capillary having an exit for ejecting a fluid;

conductive means positioned downstream from said exit;

gas flow means for establishing a region of gas, at least immediately about said exit;

voltage supply means for creating a potential difference between said exit and said conductive means, said potential difference being sufficient both to create a cone-jet of said fluid at said exit and to ionize said region of gas about said exit so as to create a stable corona discharge thereat and a current between said exit and said conductive means during flow of said fluid, said current exhibiting an elevated value upon establishment of said corona discharge.

2. The electrospray apparatus as recited in claim 1, wherein said gas flow means comprises:

a conduit that encompasses said conductive capillary, is coaxial therewith and establishes an extended flow annulus thereabout; and a gas source for introducing a flow of said gas into said flow annulus.

3. The electrospray apparatus as recited in claim 1, wherein said gas is carbon dioxide.

4. The electrospray apparatus as recited in claim 1, wherein said conductive means is a substrate having at least one orifice formed therein for enabling passage of an aerosol produced from said fluid.

5. The electrospray apparatus as recited in claim 4, further comprising:

charge means positioned on a downstream side of said substrate for rendering particles in said aerosol that pass through said one orifice to a neutral charge state.

6. The electrospray apparatus as recited in claim 1, wherein said capillary is a conductive metal tube.

7. A method for controlling an electrospray apparatus, said electrospray apparatus including a capillary having an exit for ejecting a fluid, an electrode positioned near said exit and connected to a source of reference potential, a gas source and a voltage supply for applying a high potential to said fluid, said method comprising the steps of establishing a region of gas from said gas source at least immediately about said exit of said capillary during ejection of said fluid; and adjusting said voltage source to create a potential difference between said exit of said capillary and said conductive electrode, said potential difference sufficient to ionize said region of gas about said exit of said capillary to create a stable corona discharge and a cone-jet of said fluid at said exit of said capillary and to create a current between said exit of said capillary and said conductive electrode which exhibits an elevated value upon establishment of said stable corona discharge.

8. The electrospray method as recited in claim 7, wherein a concentric conduit encompasses said conductive capillary, is coaxial therewith and establishes an extended flow annulus thereabout, said establishing step causing said gas source to introduce a flow of said gas into said flow annulus.

9. The electrospray method as recited in claim 7, wherein said gas source comprises a source of carbon dioxide.

10. The electrospray method as recited in claim 7, wherein said conductive electrode has at least one orifice formed therein for enabling passage of an aerosol produced from said fluid, said method comprising the further step of:

on a downstream side of said conductive electrode, rendering particles in said aerosol that pass through said one orifice to a neutral charge state.

* * * * *